(12) United States Patent
Ichikawa et al.

(10) Patent No.: US 12,152,166 B2
(45) Date of Patent: Nov. 26, 2024

(54) WET COATING AGENT FOR FINE PARTICLES

(71) Applicants: Nippon Soda Co., Ltd., Tokyo (JP); KOBE GAKUIN EDUCATIONAL FOUNDATION, Kobe (JP)

(72) Inventors: Hideki Ichikawa, Takasago (JP); Tooru Andoh, Kobe (JP); Yuki Uchida, Kobe (JP); Takato Nakagawa, Nishinomiya (JP)

(73) Assignees: Nippon Soda Co., Ltd., Tokyo (JP); KOBE GAKUIN EDUCATIONAL FOUNDATION, Kobe (JP)

( * ) Notice: Subject to any disclaimer, the term of this patent is extended or adjusted under 35 U.S.C. 154(b) by 373 days.

(21) Appl. No.: 17/614,976

(22) PCT Filed: Jun. 2, 2020

(86) PCT No.: PCT/JP2020/021762
§ 371 (c)(1),
(2) Date: Nov. 29, 2021

(87) PCT Pub. No.: WO2020/246463
PCT Pub. Date: Dec. 10, 2020

(65) Prior Publication Data
US 2022/0243077 A1  Aug. 4, 2022

(30) Foreign Application Priority Data
Jun. 7, 2019 (JP) .................................. 2019-106702

(51) Int. Cl.
C09D 7/65 (2018.01)
C09D 5/02 (2006.01)
C09D 7/40 (2018.01)

(52) U.S. Cl.
CPC ............... *C09D 7/65* (2018.01); *C09D 5/02* (2013.01); *C09D 7/67* (2018.01)

(58) Field of Classification Search
None
See application file for complete search history.

(56) References Cited

U.S. PATENT DOCUMENTS

| | | | |
|---|---|---|---|
| 9,775,815 B2 | 10/2017 | Schattka et al. | |
| 2008/0193522 A1 | 8/2008 | Meier et al. | |
| 2014/0141092 A1* | 5/2014 | Schattka | A61K 9/2846 514/263.36 |

FOREIGN PATENT DOCUMENTS

| | | |
|---|---|---|
| CN | 103221038 A | 7/2013 |
| CN | 104650283 A | 5/2015 |
| GB | 1 278 816 A | 6/1972 |
| GB | 2 220 142 A | 1/1990 |
| JP | 02-048521 A | 2/1990 |
| JP | 2007-099897 A | 4/2007 |
| JP | 2013-537896 A | 10/2013 |
| JP | 2014-517020 A | 7/2014 |
| WO | WO-2006/125483 A1 | 11/2006 |

OTHER PUBLICATIONS

Hu Xuegui, "Polymer Chemistry and Technology," Chemical Industry Press Co., Ltd., May 30, 1991, 99-100.
Office Action and Search Report dated Nov. 23, 2022 in CN 202080040802.9, with English translation of Search Report.
Supplementary European Search Report dated May 9, 2023 in EP 20819370.6.
Fukumori et al., "Coating of Pharmaceutical Powders by Fluidized Bed Process. IV. Softening Temperature of Acrylic Copolymers and Its Relation to Film-Formation in Aqueous Coating," Chem. Pharm. Bull., 1988, 36(12):4927-4932.
Fukumori, Yoshinobu Ph.D., "Manufacturing Process of Pharmaceutical Microparticles Assisted with Nano-structure Construction," The Micrometrics, 2006/2007, 50:3-10, with partial English translation.
Ichikawa et al., "Coating of Pharmaceutical Powders by Fluidized Bed Process. V. Agglomeration and Efficiency in the Coating with Aqueous Latices of Copoly(Ethyl Acrylate-Methyl Methacrylate-2-Hydroxyethyl Methacrylate)," Chem. Pharm. Bull, 1993, 41(6):1132-1136.
Ichikawa et al., "Coating of Pharmaceutical Powders by Fluidized Bed Process. VI. Microencapsulation Using Blend and Composite Latices of Copoly(EthylAcrylate-Methyl Methacrylate-2-Hydroxyethyl Methacrylate)," Chem. Pharm. Bull., 1994, 42(6):1308-1314.
International Search Report dated Jul. 28, 2020 in PCT/JP2020/021762.
Office Action dated Mar. 10, 2022 in CN 202080040802.9, with English translation of search report.
Office Action dated Jan. 12, 2022 in IN 202147054725.

\* cited by examiner

*Primary Examiner* — Sheeba Ahmed
(74) *Attorney, Agent, or Firm* — FITCH, EVEN, TABIN & FLANNERY, LLP (57) ABSTRACT

This wet coating agent for fine particles comprises a latex including particles that comprises a (meth)acrylate copolymer and have a 50% diameter of 10 nm to 150 nm in a volume-based particle size distribution, said (meth)acrylate copolymer being obtained by including a monomer unit derived from ethyl acrylate, a monomer unit derived from methyl methacrylate, and a monomer unit derived from 2-hydroxyethyl methacrylate.

2 Claims, 4 Drawing Sheets

WET COATING AGENT FOR FINE PARTICLES

CROSS-REFERENCE TO RELATED APPLICATIONS

This application is the U.S. National Stage of PCT/JP2020/021762, filed Jun. 2, 2020, which claims priority to Japanese Patent Application No. 2019-106702, filed Jun. 7, 2019, the content of which is incorporated herein by reference.

TECHNICAL FIELD

The present invention relates to a wet coating agent for fine particles.

Priority is claimed on Japanese Patent Application No. 2019-106702, filed Jun. 7, 2019, the content of which is incorporated herein by reference.

BACKGROUND OF THE INVENTION

A coating process is often used for the formulation of medical drugs, agricultural chemicals and the like. Nanoparticles and an aqueous dispersant thereof have been used for a coating agent, and in particular, an aqueous dispersant of polymer nanoparticles prepared by an emulsion polymerization method, an emulsification process or the like has been widely used.

For example, Patent Document 1 discloses a drug film coating method which is performed by using an aqueous latex dispersion liquid composed of a copolymer of ethyl acrylate and methacrylic acid or ethyl acrylate and methyl methacrylate as a film forming material.

Non-Patent Document 1 and Non-Patent Document 2 disclose coating with an aqueous polymer nanoparticle dispersant. A latex containing core shell nanoparticles having a core composed of 12:6:4 poly(ethyl acrylate (EA)/methyl methacrylate (MMA)/2-hydroxyethyl methacrylate (HEMA)) and a shell composed of 6:12:8 poly(EA/MMA/HEMA) as nanoparticles has been disclosed.

DOCUMENTS OF RELATED ART

Patent Documents

Patent Document 1: Japanese Unexamined Patent Application, First Publication No. Hei 2-48521

Non-Patent Documents

Non-Patent Document 1: Yoshinobu Fukumori "Manufacturing Process of Pharmaceutical Microparticles Assisted with Nano-structure Construction" The Micromeritics No. 50 (2006/2007)

Non-Patent Document 2:Ichikawa et al. "Coating of Pharmaceutical Powders by Fluidized Bed Process. VI. Microencapsulation Using Blend and Composite Latices of Copoly(Ethyl Acrylate-Methyl Methacrylate-2-Hydroxyethyl Methacrylate)" Chem. Pharm. Bull., 42, 1308 (1994).

SUMMARY OF THE INVENTION

Problems to be Solved by the Invention

An object of the present invention is to provide a wet coating agent for fine particles that can exhibit a desired property (for example, drug release control) in a smooth thin film while preventing the particle aggregation during coating.

Means to Solve the Problems

As a result of intensive studies in order to solve the above problems, the present invention including the following embodiments has been completed.

[1] A wet coating agent for fine particles, the agent including a latex containing a particle including a (meth)acrylate copolymer and having a 50% diameter of 10 nm or more and 150 nm or less in a volume based particle size distribution.

[2] The wet coating agent for fine particles according to [1], wherein the (meth)acrylate copolymer contains a monomer unit derived from ethyl acrylate, a monomer unit derived from methyl methacrylate, and a monomer unit derived from 2-hydroxyethyl methacrylate.

[3] The wet coating agent for fine particles according to [1] or [2], wherein the 50% diameter in the volume based particle size distribution is 10 nm or more and less than 40 nm.

[4] The wet coating agent for fine particles according to any one of [1] to [3], wherein the fine particle is a nuclear particle.

Effects of the Invention

The coating agent for fine particles of the present invention can form a smooth film surface and exhibit excellent controlled release properties.

EMBODIMENTS FOR CARRYING OUT THE INVENTION

A wet coating agent for fine particles of the present invention contains a latex containing particles including a (meth)acrylate copolymer.

The latex containing particles including a (meth)acrylate copolymer can be obtained, for example, by subjecting a (meth)acrylate-based monomer to a polymerization reaction by an emulsion polymerization method, or by dispersing in water a copolymer obtained by subjecting the (meth)acrylate-based monomer to a polymerization reaction by a solution polymerization method. Of these, the emulsion polymerization method is preferable.

When producing a latex, additional monomers may be further added into an emulsion polymerization reaction system. For example, a method in which a portion of the monomers is collectively charged in advance into an emulsion polymerization system and polymerized, and then the remaining monomers are continuously or intermittently added thereto to conduct polymerization can be mentioned. Copolymer particles having a core shell structure can also be obtained by making the composition of the monomers to be charged first and the composition of the monomers to be additionally added different. Further, a method in which the monomers are continuously or intermittently added from the beginning may be employed. In a step of adding the monomers, it is also possible to use a so-called power feed method in which the composition of the monomers changes continuously.

Examples of the (meth)acrylate-based monomer include a (meth)acrylate containing a linear or branched alkyl group such as methyl (meth)acrylate, ethyl (meth)acrylate, n-propyl (meth)acrylate, n-butyl (meth)acrylate, i-butyl (meth) acrylate, tert-butyl (meth)acrylate, n-pentyl (meth)acrylate, n-hexyl (meth)acrylate, 2-ethylhexyl (meth)acrylate, lauryl (meth)acrylate, isodecyl (meth)acrylate, and stearyl (meth) acrylate; hydroxyalkyl (meth)acrylates such as 2-hydroxyethyl (meth)acrylate, 2-hydroxypropyl (meth)acrylate, 3-hydroxypropyl (meth)acrylate, and hydroxybutyl (meth) acrylate; alkoxyalkyl (meth)acrylates such as 2-methoxyethyl (meth)acrylate and 2-ethoxyethyl (meth) acrylate; perfluoroalkyl (meth)acrylates, N,N-diethylaminoethyl (meth)acrylate; alicyclic (meth)acrylates such as tert-butylcyclohexyl (meth)acrylate, isobornyl (meth)acrylate, dicyclopentenyloxypropyl (meth)acrylate, dicyclopentenyl (meth)acrylate, dicyclopentenyloxyethyl (meth)acrylate; allyl (meth)acrylate, ethylene glycol di(meth)acrylate, triethylene glycol di(meth)acrylate, tetraethylene glycol di(meth)acrylate, 1,3-butylene glycol di(meth)acrylate, trimethylolpropane tri(meth)acrylate, 1,4-butanediol di(meth)acrylate, neopentyl glycol di(meth)acrylate, 1,6-hexanediol di(meth)acrylate, pentaerythritol di(meth)acrylate, pentaerythritol tetra(meth)acrylate, glycerol di(meth)acrylate, 1,1,1-trishydroxymethylethane di(meth)acrylate, 1,1,1-trishydroxymethylethane tri(meth)acrylate, and 1,1,1-trishydroxymethylpropane tri(meth)acrylate. One type of these may be used alone, or two or more types thereof may be used in combination. The monomer unit derived from the (meth) acrylate-based monomer is preferably 98% by mass or more, more preferably 99% by mass or more, and still more preferably 100% by mass with respect to the total mass of the (meth)acrylate copolymer.

A monomer other than the (meth)acrylate-based monomer can be used in an amount within a range that does not impair the effects of the present invention. Examples thereof include vinyl ester compounds such as vinyl acetate and vinyl propionate; (meth)acrolein, formylstyrol, vinyl methyl ketone, vinyl ethyl ketone, and vinyl butyl ketone; styrene; conjugated diene-based monomers such as 1,3-butadiene, isoprene, and 2-chloro-1,3-butadiene; vinyl cyanide-based monomers such as acrylonitrile, methacrylonitrile and α-chloroacrylonitrile; monobasic ethylene-based unsaturated carboxylic acid monomers such as acrylic acid and methacrylic acid, and dibasic ethylene-based unsaturated carboxylic acid monomers such as itaconic acid, maleic acid, and fumaric acid. One type of these may be used alone, or two or more types thereof may be used in combination. The monomer unit derived from a monomer other than the (meth)acrylate-based monomer is preferably 2% by mass or less, more preferably 1% by mass or less, and still more preferably 0% by mass with respect to the total mass of the (meth)acrylate copolymer.

In the present invention, the (meth)acrylate copolymer preferably contains a monomer unit derived from ethyl acrylate, a monomer unit derived from methyl methacrylate, and a monomer unit derived from 2-hydroxyethyl methacrylate.

The amount of the monomer unit derived from ethyl acrylate is preferably from 26 to 39% by mass and more preferably from 30 to 35% by mass, the amount of the monomer unit derived from methyl methacrylate is preferably from 39 to 52% by mass and more preferably from 43 to 48% by mass, and the amount of the monomer unit derived from 2-hydroxyethyl methacrylate is preferably from 9 to 35% by mass and more preferably from 17 to 27% by mass, with respect to the total mass of the (meth)acrylate copolymer. The combined total amount of the monomer units derived from ethyl acrylate, the monomer units derived from methyl methacrylate and the monomer units derived from 2-hydroxyethyl methacrylate is preferably 99% by mass or more, and more preferably 100% by mass, with respect to the total mass of the (meth)acrylate copolymers.

The latex containing particles including a (meth)acrylate copolymer has a 50% diameter of 10 nm or more and 150 nm or less, and preferably 10 nm or more and less than 40 nm in a volume based particle size distribution. By ensuring that the 50% diameter is within the above range, a coating layer having excellent cohesion resistance, surface smoothness, controlled release properties and the like can be obtained.

The 50% diameter can be adjusted by controlling the amount of the emulsifier used or by using a known seed polymerization method when produced by an emulsion polymerization method. As the seed polymerization method, a method such as an internal seed method in which a latex containing a copolymer is polymerized in the same reaction system after producing a seed, or an external seed method using a separately produced seed can be appropriately selected and used.

Here, as an emulsifier to be used, for example, a non-reactive emulsifier such as an anionic emulsifier, a cationic emulsifier, an amphoteric emulsifier, or a nonionic emulsifier, or a reactive emulsifier such as an anionic reactive emulsifier into which an ethylenic double bond has been introduced in the chemical structure of an emulsifier having both a hydrophilic group and a lipophilic group or a nonionic reactive emulsifier can be mentioned. Conventionally known emulsifiers can be used as these emulsifiers.

Examples of the anionic emulsifiers that are non-reactive emulsifiers include non-reactive alkylsulfuric acid esters, polyoxyethylene alkyl ether sulfuric acid ester salts, alkylsulfonic acid salts, alkylbenzenesulfonic acid salts, alkylnaphthalenesulfonic acid salts, alkylsulfosuccinic acid salts, alkyldiphenylether disulfonic acid salts, naphthalenesulfonate formalin condensates, polyoxyethylene polycyclic phenyl ether sulfuric acid ester salts, polyoxyethylene distyrene-modified phenyl ether sulfuric acid ester salts, fatty acid salts, alkyl phosphoric acid salts, and polyoxyethylene alkyl phenyl ether sulfuric acid ester salts. Among these, alkylsulfonic acid salts such as sodium dodecyl sulfonate are preferable.

Examples of the cationic emulsifiers that are non-reactive emulsifiers include alkylammonium salts such as dodecylammonium chloride, and quaternary ammonium salts. Examples of the amphoteric emulsifiers that are non-reactive emulsifiers include betaine ester type emulsifiers.

Examples of the nonionic emulsifiers that are non-reactive emulsifiers include non-reactive polyoxyethylene alkyl ethers, polyoxyalkylene alkyl ethers, polyoxyethylene polycyclic phenyl ethers, polyoxyethylene distyrene-modified phenyl ethers, sorbitan fatty acid esters, polyoxyethylene sorbitan fatty acid esters, polyoxyethylene sorbitol fatty acid esters, glycerin fatty acid esters, polyoxyethylene fatty acid esters, polyoxyethylene alkylamines, alkyl alkanolamides, and polyoxyethylene alkyl phenyl ethers.

The anionic reactive emulsifier that is a reactive emulsifier is, for example, an ethylenically unsaturated monomer having a sulfonic acid group, a sulfonate group or a sulfuric acid ester group and a salt thereof, and is preferably a compound having a sulfonic acid group or a group that is an ammonium salt or alkali metal salt thereof (ammonium sulfonate group or alkali metal sulfonate group). Specific examples thereof include alkylallylsulfosuccinic acid salts (such as, "Eleminol (trademark) JS-2" and "Eleminol (trademark) JS-5" manufactured by Sanyo Chemical Industries, Ltd.; and "Latemul (trademark)S-120", "Latemul (trademark)S-180A" and "Latemul (trademark) S-180" manufactured by Kao Corporation); polyoxyethylene alkyl propenyl phenyl ether sulfuric acid ester salts (such as "Aqualon (trademark) HS-10" and "Aqualon (trademark) HS-1025" manufactured by Dai-ichi Kogyo Seiyaku Co., Ltd.); α-[1-[(allyloxy)methyl]-2-(nonylphenoxy)ethyl]-ω-polyoxyethylene sulfuric acid ester salts (such as "Adeka Reasoap (trademark) SE-1025N" manufactured by Adeka Corporation); and ammonium=α-sulfonato-ω-1-(allyloxymethyl)alkyloxypolyoxy ethylenes (such as "Aqualon KH-10" manufactured by Dai-ichi Kogyo Seiyaku Co., Ltd.).

Examples of the nonionic reactive emulsifiers that are reactive emulsifiers include α-[1-[(allyloxy)methyl]-2-(nonylphenoxy)ethyl]-ω-hydroxypolyoxyethylenes (such as, "Adeka Reasoap NE-20", "Adeka Reasoap NE-30" and "Adeka Reasoap (trademark) NE-40" manufactured by Adeka Corporation); and polyoxyethylene alkyl propenyl phenyl ethers (such as "Aqualon (trademark) RN-10", "Aqualon (trademark) RN-20", "Aqualon (trademark) RN-30" and "Aqualon (trademark) RN-50" manufactured by Dai-ichi Kogyo Seiyaku Co., Ltd.).

One type of these emulsifiers may be used alone, or two or more types thereof may be used in combination.

The amount of the emulsifier used is preferably from 0.06 to 13.3 parts by mass, more preferably from 1.3 to 10 parts by mass, still more preferably from 2.7 to 6.6 parts by mass, and still more preferably from 4.0 to 5.3 parts by mass with respect to 100 parts by mass of the monomer initially charged into the reaction system.

A polymerization initiator, preferably a radical polymerization initiator, is used in order to initiate a polymerization reaction. As the polymerization initiator, either an inorganic initiator or an organic initiator can be used. Examples of the polymerization initiator used in the present invention include peroxydisulfuric acid salts, peroxides, and azobis compounds. Specific examples of such an initiator include potassium peroxodisulfate, sodium peroxodisulfate, ammonium peroxodisulfate, hydrogen peroxide, tert-butyl hydroperoxide, benzoyl peroxide, 2,2-azobisbutyronitrile, and cumene hydroperoxide. Among these, peroxydisulfuric acid salts such as ammonium peroxodisulfate are preferably used. One type of these may be used alone, or two or more types thereof may be used in combination.

The amount of the polymerization initiator used is preferably from 0.05 to 0.35 parts by mass, and more preferably from 0.05 to 1.5 parts by mass, with respect to 100 parts by mass of the monomer initially charged into the reaction system.

Further, a reducing agent such as acidic sodium sulfite, ascorbic acid or a salt thereof, erythorbic acid or a salt thereof, or Rongalite may be used in combination with the above-mentioned radical initiator. That is, a so-called redox polymerization method can also be used.

When producing a latex, the polymerization temperature is preferably from 40 to 95° C., more preferably from 45 to 90° C., and still more preferably from 55 to 85° C.

Further, the polymerization initiator is preferably added to a mixed solution containing the monomer and the emulsifier over about 1 to 5 hours with stirring.

Furthermore, after the completion of the polymerization reaction, a purification treatment such as dialysis can be carried out.

The polymerized solid content in the reaction system when producing a latex is preferably from 10 to 60% by mass, and more preferably from 20 to 40% by mass, from the viewpoints of production efficiency and particle size control during emulsion polymerization. The polymerized solid content is a solid content at the time of polymerization completion, and more specifically, refers to a ratio of the mass of the solid content after drying (including water-soluble substances) with respect to the mass of the latex before drying (including non-solid components such as water).

When producing the latex of the present embodiment, various known polymerization regulators can be used during emulsion polymerization or at the end of emulsion polymerization, as needed. Examples of such a polymerization regulator include a pH regulator and a chelating agent.

Examples of the pH regulator include sodium hydroxide, potassium hydroxide, ammonium hydroxide, sodium hydrogen carbonate, disodium hydrogen phosphate, and amines such as monoethanolamine, dimethylethanolamine, triethanolamine and triethylamine. Among these, ammonium hydroxide and amines such as monoethanolamine, dimethylethanolamine, triethanolamine and triethylamine are preferable. One type of these may be used alone, or two or more types thereof may be used in combination.

Examples of the chelating agent include sodium ethylenediaminetetraacetate.

The number average molecular weight of the (meth) acrylate copolymer is preferably from 5,000 to 5,000,000, more preferably from 50,000 to 4,000,000, still more preferably from 80,000 to 3,000,000, and still more preferably from 100,000 to 1,000,000. Examples of the method for controlling the number average molecular weight include a method of adjusting the amount of the initiator used, the polymerization temperature, the amount of the monomer fed, the amount of the chain transfer agent, or the like, and among these, a method of adjusting the amount of the chain transfer agent can be mentioned as a more preferable method.

The molecular weight distribution (ratio of weight average molecular weight/number average molecular weight) of the (meth)acrylate copolymer is not particularly limited, but is preferably from 1.5 to 10.0, more preferably from 1.7 to 9.0, and still more preferably from 1.8 to 8.0. The molecular weight distribution can be controlled by a known method, and a method of controlling the polymerization reaction by adding the chain transfer agent on several separate occasions can be mentioned as a preferred method.

Examples of the chain transfer agent include mercaptan-based compounds such as n-butyl mercaptan, tert-butyl mercaptan, tert-dodecyl mercaptan, n-octyl mercaptan and n-lauryl mercaptan, and dimers of nuclear-substituted α-methylstyrene such as α-methylstyrene dimers; disulfides such as tetramethylthiuram disulfide and tetraethylthiuram disulfide; halogenated derivatives such as carbon tetrachloride and carbon tetrabromide; and 2-ethylhexylthioglycolate. Among these, mercaptans are preferable. One type of these may be used alone, or two or more types thereof may be used in combination.

The amount of the chain transfer agent used is preferably from 0.1 to 2.50 parts by mass, and more preferably from 0.15 to 2.50 parts by mass with respect to 100 parts by mass of all the monomers.

A method for adding the chain transfer agent is not particularly limited, and a known method can be employed. For example, collective addition, batch addition, or continuous addition can be employed.

The glass transition temperature of the (meth)acrylate copolymer is preferably from 20 to 90° C., more preferably from 25 to 80° C., and still more preferably from 30 to 70° C. The glass transition temperature of the copolymer can be measured in accordance with ASTM D3418-97.

The fine particles (nuclear particles) to which the wet coating agent of the present invention may be applied are not particularly limited. The nuclear particles used in the present invention may be particles composed of an active ingredient itself (for example, a drug in the case of a medical drug or an agricultural chemical), particles composed of a mixture of a carrier and a drug, particles in which the surface of a carrier (core particle) is covered with a drug, or particles composed of a drug-free carrier. The nuclear particles can be used without any particular limitation as long as they do not lose their shape during operation. The nuclear particles are not particularly limited by the volume average particle size, but those having a volume average particle diameter of 30 to 1,000 μm are preferable, and those having a volume average particle diameter of 50 to 500 μm are more preferable.

Examples of the nuclear particles include pills, granules, powders, single crystals of drugs, aggregates of drug powders, lactose particles, hydroxyapatite, calcium carbonate particles; and crystalline cellulose granules, spherical sucrose granules, and spherical mannitol granules, which are commercially available as coated nuclear particles in the field of pharmaceutical formulations.

The nuclear particles may be a controlled release formulation such as a rapid release formulation and a continuous release formulation (sustained release formulation). The nuclear particles may contain a conventional additive. Examples of the additive include diluents, disintegrants, binders, lubricants, colorants, pH regulators, pH buffers, surfactants, sustained release agents, stabilizers, acidulants, fragrances, fluidizers, refreshing agents, sweeteners, umami components and sweetness enhancers. These additives are used in conventional amounts in the field of pharmaceutical formulations.

Examples of drugs that are active ingredients of medical drugs include analgesics, antipyretic analgesics, headache remedies, antitussives, expectorants, sedatives, antispasmodics, antihistamines, antiallergic agents, antiplasmin agents, bronchodilators, asthma medications, diabetes medications, agents for liver disease, anti-ulcer agents, drugs for gastritis, stomachics and digestants, gastrointestinal motility activators, antihypertensive drugs, antianginal drugs, hypotensive agents, antihypotensive drugs, lipid lowering drugs, hormone drugs, antibiotics, antiviral agents, sulfa drugs, anti-inflammatory drugs, psychotropic drugs, intraocular pressure lowering agents, antiemetics, antidiarrheal agents, gout remedies, antiarrhythmics, vasoconstrictors, digestives, sleep or hypnotic inducers (inducing drugs), sympathetic blocking agents, anemia drugs, antiepileptic drugs, antivertiginous drugs, disequilibrium drugs, tuberculosis drugs, vitamin deficiency drugs, antidementia drugs, drugs for the treatment of urinary incontinence, antidizziness drugs, oral disinfectants, parasiticides, vitamin supplements, amino acids, and minerals. More specific examples thereof include agents affecting the central nervous system (such as acetaminophen, aspirin, indomethacin, ibuprofen, naproxen, diclofenac sodium, meclofenoxate hydrochloride, chlorpromazine, tolmetin sodium, milnacipran hydrochloride, and phenobarbital), agents affecting the peripheral nervous system (such as etomidoline, tolperisone hydrochloride, pipethanate ethobromide, methylbenactyzium bromide, and flopropione), hemostatics (such as carbazochrome sodium sulfonate, and protamine sulfate), cardiovascular drugs (such as aminophylline, etilefrine hydrochloride, diltiazem hydrochloride, digitoxin, and captopril), agents affecting respiratory organs (such as ephedrine hydrochloride, clorprenaline hydrochloride, oxeladin citrate, cloperastine, and sodium cromoglycate), agents affecting digestive organs (such as berberine chloride, loperamide hydrochloride, cimetidine, ranitidine hydrochloride, and famotidine), coronary vasodilators (such as nifedipine, nicardipine, and verapamil), vitamin supplements (such as ascorbic acid, thiamine hydrochloride, calcium pantothenate, and riboflavin butyrate), preparations for metabolic diseases (such as camostat mesilate, mizoribine, and lysozyme chloride), drugs for allergies (such as cyproheptadine hydrochloride, diphenhydramine hydrochloride, alimemazine tartrate, suplatast tosilate, and diphenhydramine maleate), chemotherapeutic agents (such as acyclovir, enoxacin, ofloxacin, pipemidic acid trihydrate, and levofloxacin), and antibiotics (such as erythromycin, cefcapene pivoxil hydrochloride, cefteram pivoxil, cefpodoxime proxetil, cefaclor, cephalexin, clarithromycin, and rokitamycin).

Examples of the drugs that are active ingredients of agricultural chemicals include antibacterial agents, antiviral agents, fungicides, acaricides, insecticides, nematicides, rodenticides, herbicides, plant growth regulators, fertilizers, and safeners.

Among the above compounds that are active ingredients of medical drugs or agricultural chemicals, compounds having a salt forming moiety also include physiologically or pharmaceutically acceptable salts thereof (particularly, medically or agrochemically acceptable salts, or the like), or the like.

Examples of the diluents include starches such as corn starch, potato starch, wheat starch, rice starch, partially pregelatinized starch, pregelatinized starch, and porous starch; sugars and sugar alcohols such as lactose, fructose, glucose, D-mannitol, sorbitol and trehalose; anhydrous calcium phosphate; crystalline cellulose; precipitated calcium carbonate; and calcium silicate.

Examples of the disintegrant include carboxymethyl cellulose, calcium carboxymethyl cellulose, sodium carboxymethyl starch, croscarmellose sodium, crospovidone, low substituted hydroxypropyl cellulose, and hydroxypropyl starch.

Examples of the binder include crystalline cellulose, hydroxypropyl cellulose, hydroxypropyl methyl cellulose, polyvinylpyrrolidone, and gum arabic powder.

Examples of the lubricant include magnesium stearate, calcium stearate, talc, sucrose fatty acid esters, and sodium stearyl fumarate.

Examples of the colorant include edible pigments such as edible yellow No. 5, edible red No. 2, and edible blue No. 2; edible lake pigments; and iron sesquioxide.

Examples of the pH regulator include citrates, phosphates, carbonates, tartrates, fumarates, acetates, and amino acid salts.

Examples of the pH buffer include citric acid-sodium citrate buffers.

Examples of the surfactant include sodium lauryl sulfate, polysorbates, and polyoxyethylene polyoxypropylene glycols.

Examples of the stabilizer include tocopherol, tetrasodium edetate, nicotinamide, and cyclodextrins.

Examples of the acidulant include ascorbic acid, citric acid, tartaric acid, and malic acid.

Examples of the fragrance include menthol, peppermint oil, lemon oil, and vanillin.

Examples of the fluidizer include light anhydrous silicic acid and hydrous silicon dioxide.

Examples of the refreshing agent include terpene-based compounds such as camphor and borneol (monoterpene alcohols and the like), as well as essential oils, essences or powders containing the above terpene-based compounds; essential oils, essences or powders of peppermint, spearmint, cool mint or the like; those obtained by causing the above essential oils or essences to adsorb on powdery carriers (such as dextrin); and those obtained by mixing essential oils or essences with diluents (such as gum Arabic) and liquid bases (such as water and alcohol), followed by granulation.

Examples of the sweeteners include non-sugar sweeteners, sugar alcohols and sugars. As a non-sugar sweetener, both synthetic sweeteners and natural sweeteners can be used.

Examples of the umami components include amino acid-based umami components (amino acids or salts thereof, such as, glutamic acid, sodium glutamate, potassium glutamate, glutamic acid hydrochloride, sodium guanylate, inosinic acid, sodium inosinate, arginine-glutamate, aspartic acid, sodium aspartate, glycine, or alanine), peptide-based umami components (dipeptides such as L-glutamyl-L-glutamic acid and L-glutamyl-L-serine; tripeptides such as tri-L-glutamic acid and L-glutamyl-L-glycyl-L-serine; and the like), and carboxylic acid-based umami components (carboxylic acid salts such as sodium succinate, and the like).

Furthermore, a sweetness enhancer (or a saltiness enhancer) having saltiness (salty taste) may be contained. Examples of such a sweetness enhancer include sodium chloride, potassium chloride, and phosphates (potassium hydrogenphosphate, sodium hydrogenphosphate, and the like). In many cases, the sweetness enhancer (or saltiness enhancer) is a neutral salt, such as a salt that dissociates as sodium ions and/or chlorine ions (chloride ions).

Examples of other components that can be contained in the nuclear particles include antioxidants or oxidation inhibitors, dispersants, suspensions, solubilizing agents, thickeners (such as water-soluble polymers such as carboxyvinyl polymers, polyvinyl alcohols and gelatin; and cellulose ethers such as carboxymethyl cellulose), antiseptics or preservatives (such as parabens such as methylparaben and butylparaben), fungicides or antimicrobial agents (such as benzoic acids such as sodium benzoate), antistatic agents, corrigents or masking agents, odor improving agents, defoaming agents, tonicity agents, and soothing agents. One type of these additives can be used alone, or two or more types thereof can be used in combination. A method for producing the nuclear particles is not particularly limited, and a general granulation method can be employed.

By causing the wet coating agent of the present invention to adhere to the surface of the nuclear particles using a spray method, coated particles composed of the nuclear particles and a thin film of a methacrylic copolymer that coats the nuclear particles can be obtained.

Hereinafter, the present invention will be described in more detail with reference to Examples. It should be noted that the Examples do not limit the scope of the present invention.

Example 1

1.38 g of sodium dodecyl sulfonate was dissolved in 300 g of distilled water. 34.6 g of a monomer composed of 27.3% by mol of ethyl acrylate, 54.5% by mol of methyl methacrylate and 18.2% by mol of 2-hydroxyethyl methacrylate was added thereto, and the resulting mixture was stirred for 5 minutes and emulsified using a homomixer (4C, manufactured by Tokushu Kika Kogyo Co., Ltd.). The resultant was transferred to a 500 mL four-necked glass flask.

While stirring at 80° C. under a nitrogen gas flow, 0.5 mL of 4% (w/v) ammonium persulfate was added dropwise to the above flask every 15 minutes for a total of 4 ml, and a polymerization reaction was carried out for 2 hours from the first dropwise addition of ammonium persulfate.

The obtained latex was dialyzed in purified water using a cellulose tube (UC17/8, manufactured by Sanko Junyaku Co., Ltd.). The water was replaced with fresh purified water every half day, and a washing operation was performed for a total of 5 days. Then, the particle size distribution of the latex was measured by a dynamic light scattering particle size distribution measuring device (LB500, manufactured by Horiba, Ltd.). The 50% diameter in the volume based particle size distribution was 28.6 nm, and the glass transition temperature Tg of the copolymer was 61.8° C. It should be noted that the glass transition temperature was measured with a differential scanning calorimeter (DSC50, manufactured by Shimadzu Corporation). The measurement conditions were as follows: sample pan was an aluminum pan; the amount of sample charged was 5 mg; and the rate of temperature increase was 20° C./min. Tg was defined as a temperature at a point of intersection obtained by extrapolating a straight portion of a baseline before the glass transition and a tangent of an inflection point of a transition region in a DSC thermogram.

Spherical nuclear particles coated with a drug (90-125 μm) were prepared. The nuclear particles were placed in a spouted bed coater equipped with a draft tube to form a fluidized bed. The obtained latex was sprayed thereto at a level of 40%, 60%, or 80% on a solid mass basis to obtain 40% coated particles, 60% coated particles, and 80% coated particles, respectively.

The obtained 80% coated particles were screened, and a rate at which the nuclear particles were bonded and aggregated with each other (aggregation rate) was calculated. The calculated aggregation rate was 0.62% at the maximum.

2% by mass of light anhydrous silicic acid (Aerosil 200) was added to and mixed with 40% coated particles, 60% coated particles, and 80% coated particles, respectively. Subsequently, the resulting mixtures were heated at 90° C. for 12 hours. Then, in accordance with the method 2 (paddle method) of the dissolution test method of the Japanese Pharmacopoeia 17th Edition, the coated particles were placed in purified water at 37° C. and stirred with a paddle at a rotational speed of 200 rpm. The results of drug dissolution are indicated by filled circles in FIG. 1. As a result, it was confirmed that each of the coated particles obtained in Example 1 was excellent in controlled release properties.

Figure 2:
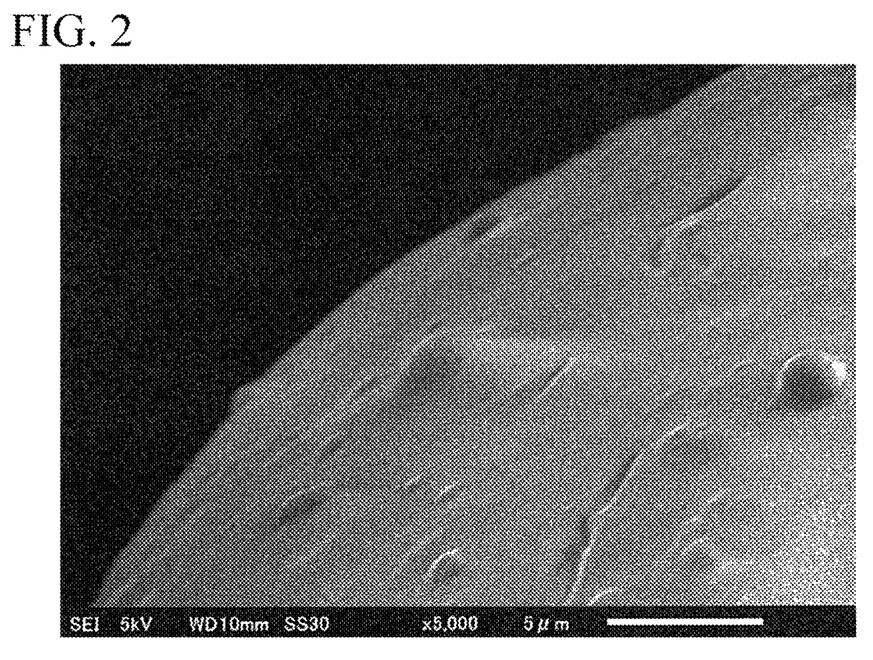
FIG. 2 is a diagram showing a SEM image of the coated particles obtained in Example 1.

FIG. 2 shows an observation result of the surface of the 80% coated particles using a scanning electron microscope (SEM). It was confirmed that the surface of the 80% coated particles obtained in Example 1 was smooth and a dense coating film was formed.

Comparative Example 1

A latex was obtained by the same method as in Example 1 except that the amount of sodium dodecyl sulfonate was changed to 0.02 g. The 50% diameter in the volume based particle size distribution was 221.1 nm, and the glass transition temperature Tg of the copolymer was 63.2° C.

40% coated particles, 60% coated particles, and 80% coated particles were obtained in the same manner as in Example 1 except that the latex obtained in Comparative Example 1 was used.

The aggregation rate of the obtained 80% coated particles was calculated. The calculated aggregation rate was 2.37% at the maximum.

Figure 1:
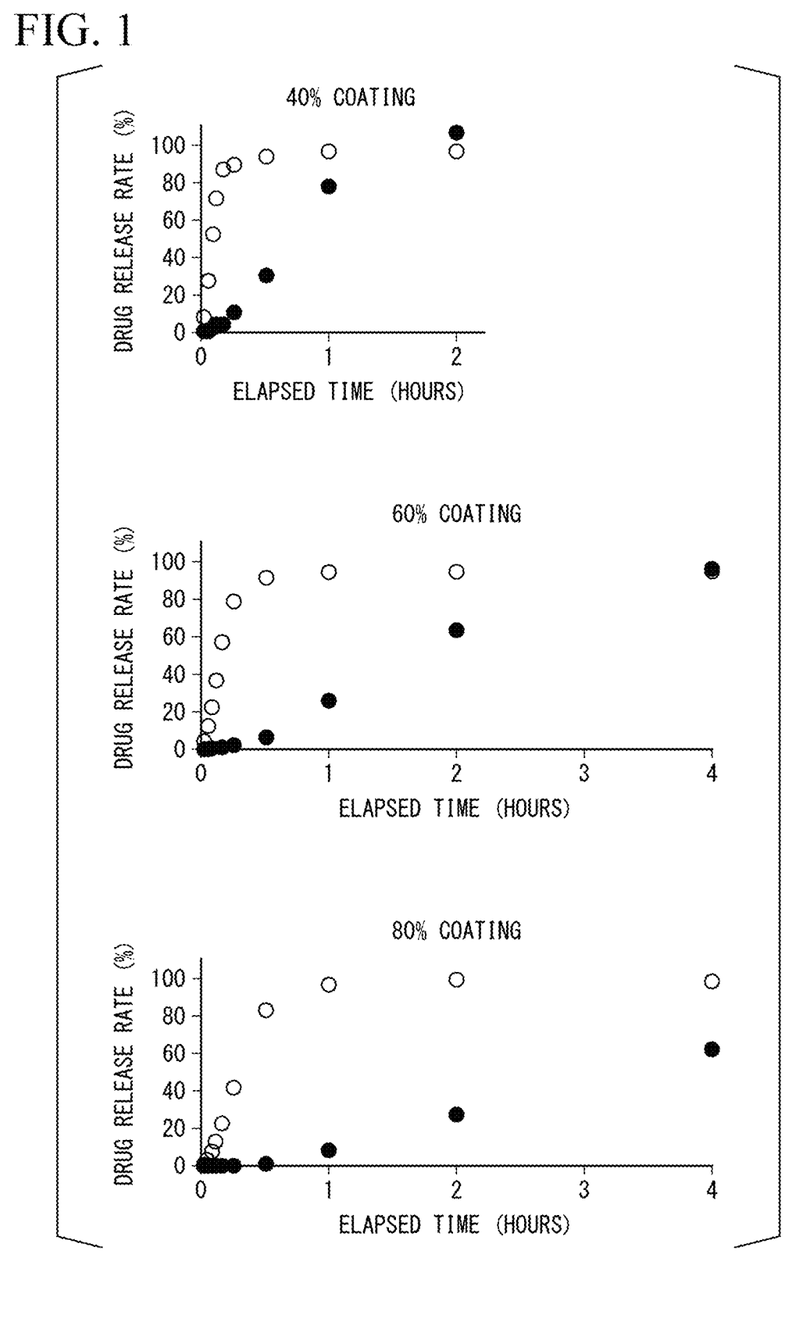
FIG. 1 is a diagram showing drug release rates of coated particles obtained in Example 1 and Comparative Example 1 with the passage of time.

The results of drug dissolution measured in the same manner as in Example 1 except that the 40% coated particles, 60% coated particles, and 80% coated particles obtained in Comparative Example 1 were used are indicated by open circles in FIG. 1. As a result, it was confirmed that each of the coated particles prepared in Comparative Example 1 was inferior to each of the coated particles prepared in Example 1 in controlled release properties.

Figure 3:
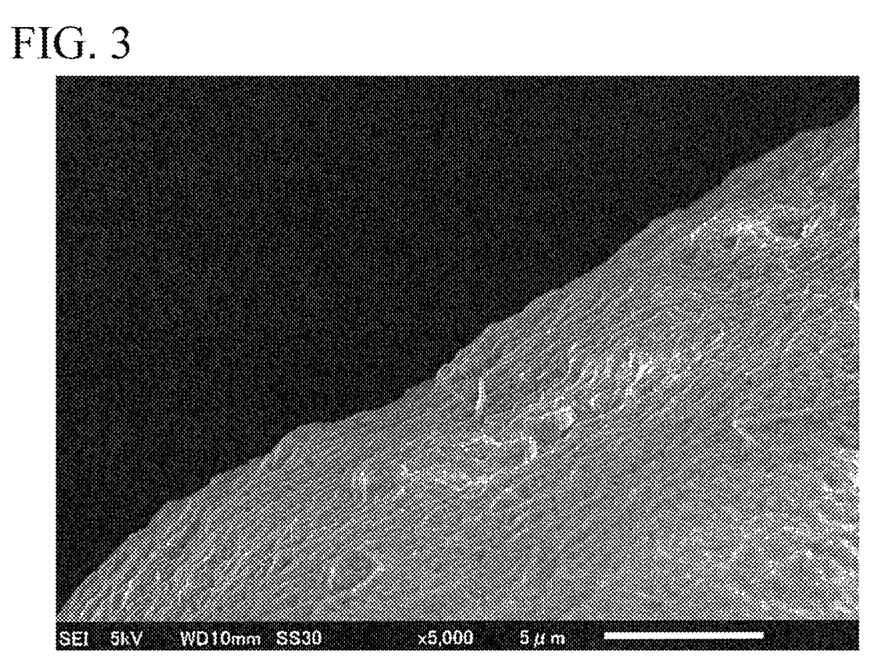
FIG. 3 is a diagram showing a SEM image of the coated particles obtained in Comparative Example 1.

FIG. 3 shows an observation result of the surface of the 80% coated particles using a scanning electron microscope (SEM) in the same manner as in Example 1. It was confirmed that the 80% coated particles obtained in Comparative Example 1 were inferior to the 80% coated particles obtained in Example 1 in surface smoothness.

Example 2

A latex was obtained by the same method as in Example 1 except that a monomer composed of 27.3% by mol of ethyl acrylate, 54.5% by mol of methyl methacrylate and 18.2% by mol of 2-hydroxyethyl methacrylate was changed to a monomer composed of 40.9% by mol of ethyl acrylate, 40.9% by mol of methyl methacrylate and 18.2% by mol of 2-hydroxyethyl methacrylate. The 50% diameter in the volume based particle size distribution was 34.6 nm, and the glass transition temperature Tg of the copolymer was 44.3° C.

Spherical nuclear particles coated with a drug (90-125 μm) were prepared. The nuclear particles were placed in a spouted bed coater equipped with a draft tube to form a fluidized bed. The obtained latex was sprayed thereto at a level of 20%, 40%, 60%, or 80% on a solid mass basis to obtain 20% coated particles, 40% coated particles, 60% coated particles, and 80% coated particles, respectively.

2% by mass of light anhydrous silicic acid (Aerosil 200) was added to and mixed with 20% coated particles, 40% coated particles, 60% coated particles, and 80% coated particles, respectively. Subsequently, the resulting mixtures were heated at 80° C. for 12 hours. Then, in accordance with the method 2 (paddle method) of the dissolution test method of the Japanese Pharmacopoeia 17th Edition, the coated particles were placed in purified water at 37° C. and stirred with a paddle at a rotational speed of 200 rpm. The results of drug dissolution are indicated by filled circles in FIG. 4.

As a result, it was confirmed that each of the coated particles was excellent in controlled release properties.

Figure 5:
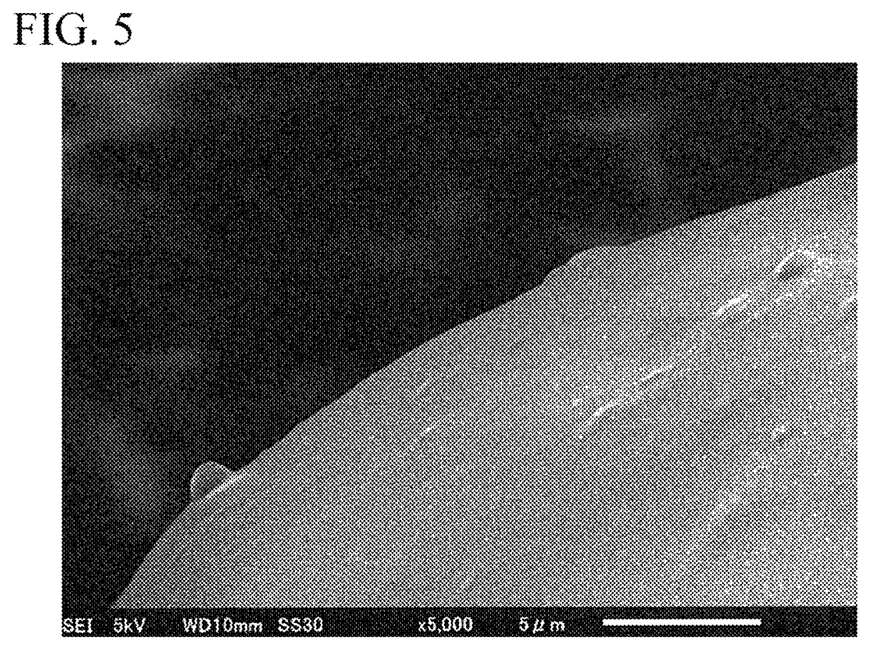
FIG. 5 is a diagram showing a SEM image of a coated particle obtained in Example 2.

FIG. 5 shows an observation result of the surface of the 80% coated particles using a scanning electron microscope (SEM). It was confirmed that the surface of the 80% coated particles obtained in Example 2 was smooth and a dense coating film was formed.

Comparative Example 2

A latex was obtained by the same method as in Example 2 except that the amount of sodium dodecyl sulfonate was changed to 0.02 g. The 50% diameter in the volume based particle size distribution was 220.1 nm, and the glass transition temperature Tg of the copolymer was 45.8° C.

20% coated particles, 40% coated particles, 60% coated particles, and 80% coated particles were obtained in the same manner as in Example 2 except that the latex obtained in Comparative Example 2 was used.

Figure 4:
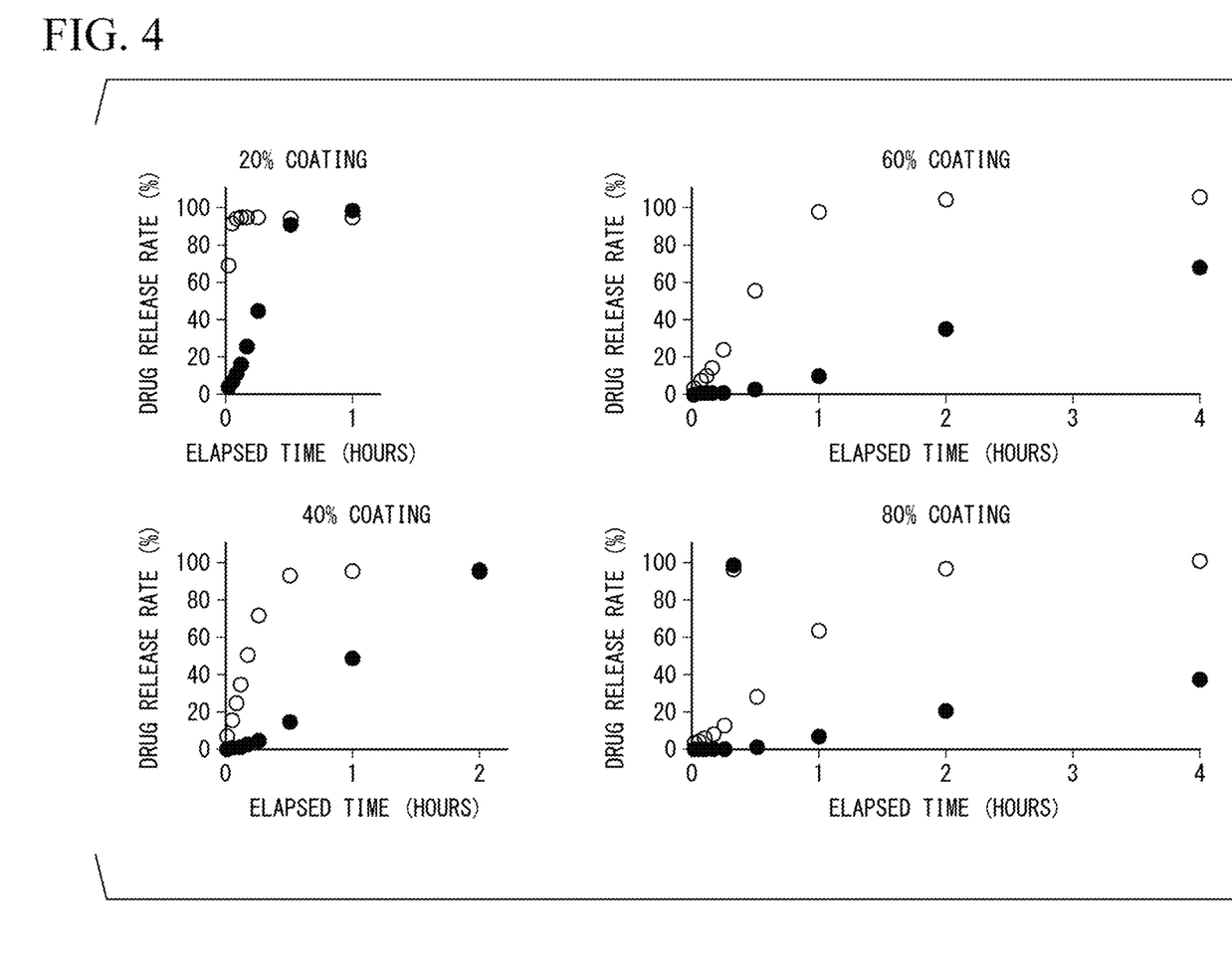
FIG. 4 is a diagram showing drug release rates of coated particles obtained in Example 2 and Comparative Example 2 with the passage of time.

The results of drug dissolution measured in the same manner as in Example 2 except that the 20% coated particles, 40% coated particles, 60% coated particles, and 80% coated particles obtained in Comparative Example 2 were used are indicated by open circles in FIG. 4.

As a result, it was confirmed that each of the coated particles prepared in Comparative Example 2 was inferior to each of the coated particles prepared in Example 2 in controlled release properties.

Figure 6:
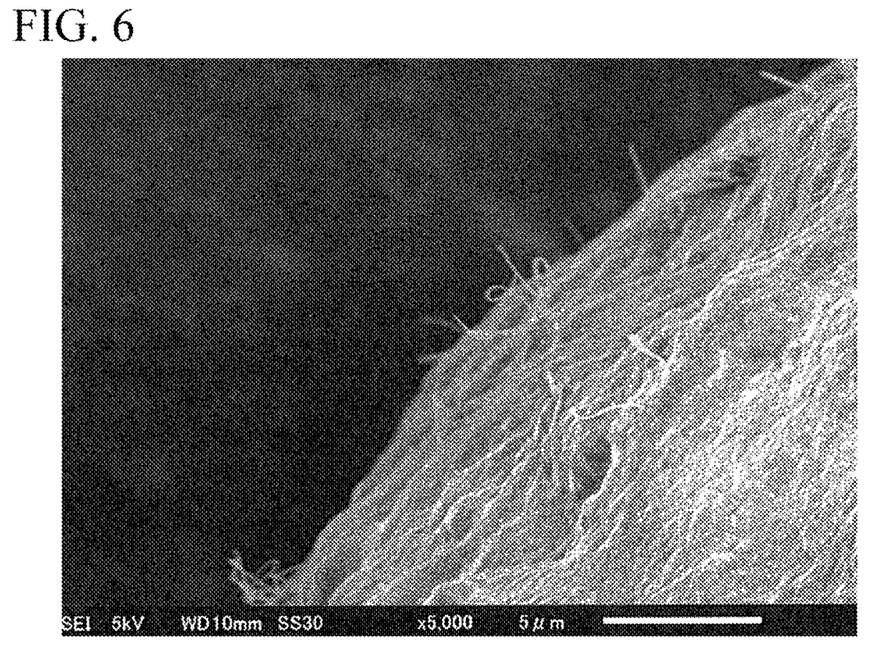
FIG. 6 is a diagram showing a SEM image of a coated particle obtained in Comparative Example 2.

FIG. 6 shows an observation result of the surface of the 80% coated particles obtained in Comparative Example 2 using a scanning electron microscope (SEM). The 80% coated particles obtained in Comparative Example 2 were inferior to the 80% coated particles obtained in Example 2 in surface smoothness.

INDUSTRIAL APPLICABILITY

The coating agent for fine particles of the present invention can form a smooth film surface and exhibit excellent controlled release properties while preventing the particle aggregation during coating.

The invention claimed is:
1. A wet coating agent for fine particles, the agent comprising a latex comprising a particle comprising a (meth) acrylate copolymer and having a 50% diameter of 28.6 nm to 34.6 nm in a volume based particle size distribution, wherein the (meth) acrylate copolymer consists of a monomer unit derived from ethyl acrylate, a monomer unit derived from methyl methacrylate, and a monomer unit derived from 2-hydroxyethyl methacrylate.
2. The wet coating agent for fine particles according to claim 1, wherein the fine particles are nuclear particles.

* * * * *